US010257429B2

(12) United States Patent
Seto

(10) Patent No.: US 10,257,429 B2
(45) Date of Patent: Apr. 9, 2019

(54) ROLLING SHUTTER IMAGING DEVICE AND ENDOSCOPE APPARATUS INCLUDING THE SAME

(71) Applicant: FUJIFILM Corporation, Tokyo (JP)

(72) Inventor: Yasuhiro Seto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 836 days.

(21) Appl. No.: 14/465,030

(22) Filed: Aug. 21, 2014

(65) Prior Publication Data

US 2014/0364690 A1   Dec. 11, 2014

Related U.S. Application Data

(63) Continuation of application No. PCT/JP2013/057256, filed on Mar. 14, 2013.

(30) Foreign Application Priority Data

Mar. 28, 2012   (JP) ................ 2012-074246

(51) Int. Cl.
*G02B 23/24*   (2006.01)
*H04N 5/225*   (2006.01)
(Continued)

(52) U.S. Cl.
CPC ......... *H04N 5/2354* (2013.01); *A61B 1/0005* (2013.01); *A61B 1/00009* (2013.01);
(Continued)

(58) Field of Classification Search
CPC ..... A61B 1/00009; A61B 1/0005; A61B 1/04; A61B 1/043; A61B 1/045; A61B 1/05;
(Continued)

(56) References Cited

U.S. PATENT DOCUMENTS 9,326,664 B2 *   5/2016   Takei ................. A61B 1/00186
9,801,530 B2 *  10/2017   Kagaya ................. A61B 1/051
(Continued)

FOREIGN PATENT DOCUMENTS

JP   61-82731 A   4/1986

OTHER PUBLICATIONS

International Search Report issued in PCT/JP2013/057256, dated Apr. 16, 2013.
(Continued)

*Primary Examiner* — John P Leubecker
*Assistant Examiner* — William B Chou
(74) *Attorney, Agent, or Firm* — Birch, Stewart, Kolasch & Birch, LLP

(57) ABSTRACT

An imaging device includes a light source capable of emitting multi-types of illumination light beams, an imaging unit including an imaging element driven by a rolling shutter method, a light source control unit, a frame image control unit, and an image generation unit. The frame image control unit controls the light source control unit and the imaging unit so as to obtain an output having a frame group, in which second exposure frames Exp2 and Exp4 are respectively disposed before and after a first exposure frame Exp3, as one period. The imaging signal generation unit generates an imaging signal according to illumination light using a ratio of a period from the exposure start timing of each horizontal pixel line to the switching timing of the illumination light and a period from the switching timing of the illumination light to the exposure end timing in the first and second exposure frames.

19 Claims, 13 Drawing Sheets

(51) Int. Cl.

| | |
|---|---|
| *H04N 5/235* | (2006.01) |
| *H04N 5/353* | (2011.01) |
| *A61B 1/00* | (2006.01) |
| *A61B 1/05* | (2006.01) |
| *A61B 1/06* | (2006.01) |
| *A61B 1/045* | (2006.01) |

(52) U.S. Cl.
CPC ............... *A61B 1/045* (2013.01); *A61B 1/05* (2013.01); *A61B 1/0638* (2013.01); *G02B 23/2461* (2013.01); *G02B 23/2484* (2013.01); *H04N 5/2256* (2013.01); *H04N 5/2353* (2013.01); *H04N 5/3537* (2013.01); *G02B 23/2469* (2013.01); *H04N 2005/2255* (2013.01)

(58) Field of Classification Search
CPC ....... A61B 1/06; A61B 1/0638; A61B 1/0661; A61B 1/0684; H04N 5/3532; G02B 23/2484; G03B 9/08
USPC ............... 600/109, 160, 178, 179, 180, 181; 348/45, 65, 69, 70, 294, 340; 25/109, 25/160, 178, 179, 180, 181
See application file for complete search history.

(56) References Cited

U.S. PATENT DOCUMENTS

| | | | | |
|---|---|---|---|---|
| 9,826,891 | B2* | 11/2017 | Kagaya | A61B 1/051 |
| 2007/0177021 | A1* | 8/2007 | Shan | H04N 5/23254 |
| | | | | 348/208.12 |
| 2009/0023991 | A1* | 1/2009 | Gono | A61B 1/00009 |
| | | | | 600/109 |
| 2011/0292183 | A1* | 12/2011 | Tajiri | H05K 999/99 |
| | | | | 348/50 |
| 2012/0016201 | A1* | 1/2012 | Seto | A61B 1/045 |
| | | | | 600/180 |
| 2014/0078277 | A1* | 3/2014 | Dai | A61B 1/00004 |
| | | | | 348/68 |
| 2014/0240468 | A1* | 8/2014 | Feke | A61B 1/0638 |
| | | | | 348/47 |
| 2016/0353972 | A1* | 12/2016 | Yano | A61B 1/045 |
| 2017/0085763 | A1* | 3/2017 | Sakai | A61B 1/06 |
| 2018/0227476 | A1* | 8/2018 | Kobayashi | A61B 1/04 |

OTHER PUBLICATIONS

Written Opinion of the International Searching Authority issued in PCT/JP2013/057256, dated Apr. 16, 2013.

* cited by examiner

ROLLING SHUTTER IMAGING DEVICE AND ENDOSCOPE APPARATUS INCLUDING THE SAME

CROSS REFERENCE TO RELATED APPLICATIONS

This application is a Continuation of PCT International Application No. PCT/JP2013/057256 filed on Mar. 14, 2013, which claims priority under 35 U.S.C § 119(a) to Patent Application No. 2012-074246 filed in Japan on Mar. 28, 2012, all of which are hereby expressly incorporated by reference into the present application.

BACKGROUND OF THE INVENTION

1. Field of the Invention

The present invention relates to an imaging device and an endoscope apparatus including the same.

2. Description of the Related Art

There is an imaging device that performs imaging based on a frame sequential method by sequentially emitting illumination light beams having different spectra to a subject in synchronization with the imaging timing. When an imaging element based on a global shutter type one-shot exposure method is used as an imaging element, a captured image that is illuminated by different illumination light for each imaging frame is obtained. An endoscope apparatus that obtains an endoscopic image by imaging based on such a frame sequential method is disclosed in JP-1986-82731A (JP-S61-82731A), for example.

SUMMARY OF THE INVENTION

In recent years, instead of a white light source such as a xenon lamp, a semiconductor light source such as a laser light source or an LED light source has been adopted as a light source due to high efficiency and easy maintenance.

In addition, a complementary metal oxide semiconductor (CMOS) type image sensor having lower power consumption and higher reading speed than a charge coupled device (CCD) type image sensor has come to be widely adopted as an imaging element. However, the CMOS type image sensor is of a rolling shutter type, and the exposure period of the horizontal pixel line differs depending on the line.

For this reason, when performing imaging based on the frame sequential method by switching a plurality of types of illumination light beams, the exposure period of a specific horizontal pixel line may pass the switching timing of illumination light depending on the emission timing of illumination light. A captured image obtained in this case becomes an unnatural image exposed by a plurality of illumination light beams, and does not become a normal captured image.

Therefore, when performing imaging based on the frame sequential method using a rolling shutter type imaging element, illumination light switching is performed in units of an imaging frame. However, when generating a composite image by combining respective images captured by a plurality of types of illumination light beams, a number of imaging frames for generating the composite image are required in the rolling shutter method compared with the global shutter method. For this reason, video responsiveness is reduced. This is disadvantageous in that color shift easily occurs in a captured image when imaging a fast moving subject.

Therefore, it is an object of the present invention to provide an imaging device excellent in color reproducibility by improving video responsiveness even when imaging based on a frame sequential method is performed by sequentially switching a plurality of types of illumination light beams using a rolling shutter type imaging element and an endoscope apparatus including the same.

An imaging device of the present invention includes: a light source capable of emitting a plurality of types of illumination light beams having different spectra; an imaging unit including an imaging element in which a plurality of pixels are arrayed in a horizontal direction and a vertical direction and which includes a plurality of horizontal pixel lines formed by pixels arrayed in the horizontal direction and is driven by a rolling shutter method; a light source control unit that performs switching between the illumination light beams emitted from the light source; a frame image control unit that generates a first exposure frame, which is formed by a unit irradiation period in which one of the illumination light beams is emitted and a unit irradiation period in which different illumination light from the illumination light beam is emitted, and a second exposure frame, which is formed by a unit irradiation period in which one of the illumination light beams is emitted and a unit irradiation period in which no illumination light is emitted, and outputs a frame group, in which the second exposure frame is set before and after the one first exposure frame or the two continuous first exposure frames, as one period; and an imaging signal generation unit that generates an imaging signal amount, which is obtained from the pixels when the pixels are exposed using the same illumination light in the unit irradiation period, using a detection signal amount read from the pixels of each of the horizontal pixel lines in each exposure frame included in the frame group.

An endoscope apparatus of the present invention includes the imaging device.

According to the present invention, even if imaging based on the frame sequential method is performed using a rolling shutter type imaging element by sequentially switching a plurality of types of illumination light beams, video responsiveness is improved. Therefore, a configuration with excellent color reproducibility can be obtained.

DESCRIPTION OF THE PREFERRED EMBODIMENTS

Hereinafter, an embodiment of the present invention will be described in detail with reference to the diagrams.

Figure 1:
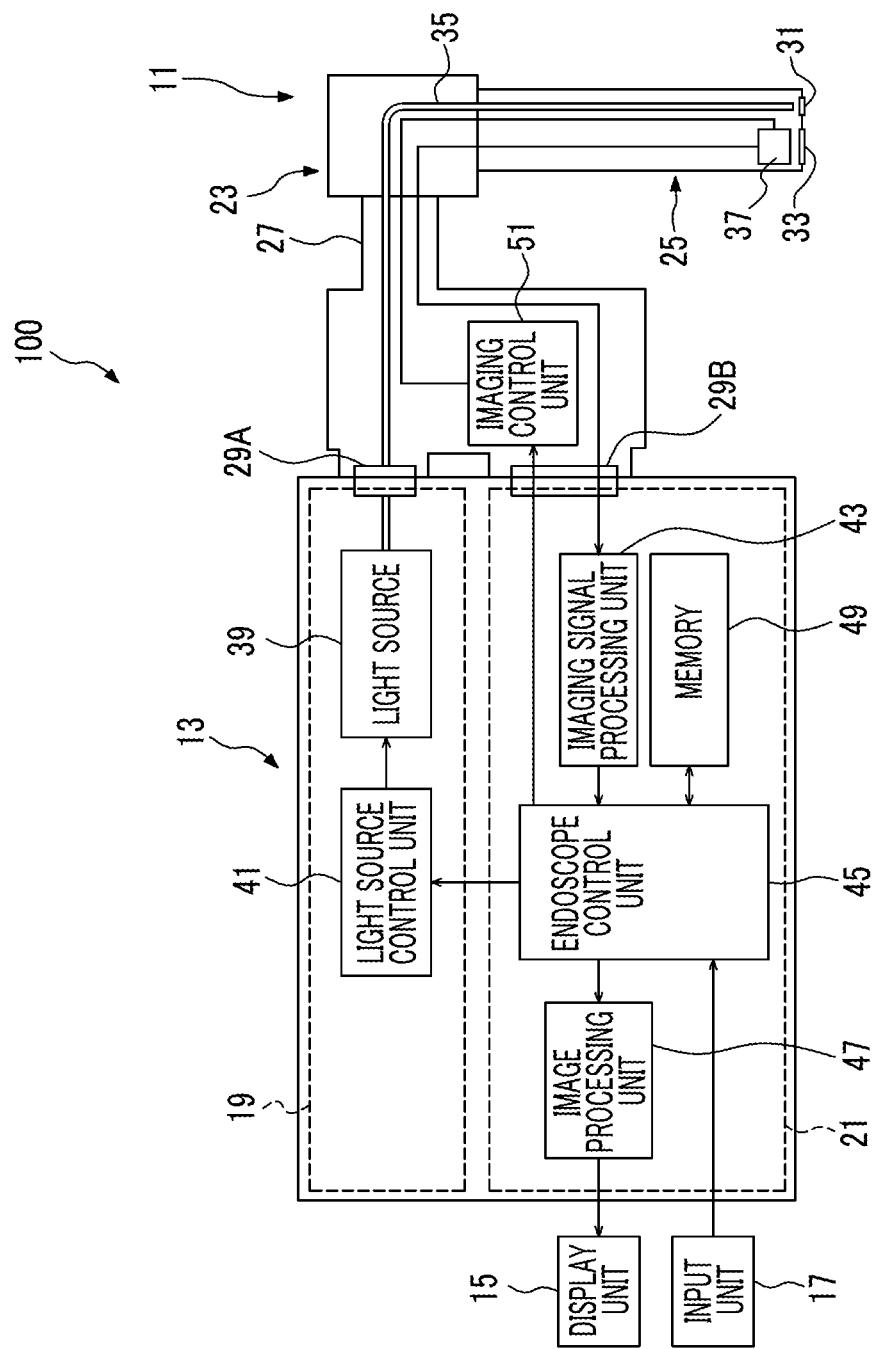
FIG. 1 is a diagram for explaining an embodiment of the present invention, and is a block diagram showing the schematic configuration of an endoscope apparatus.
Figure 2:
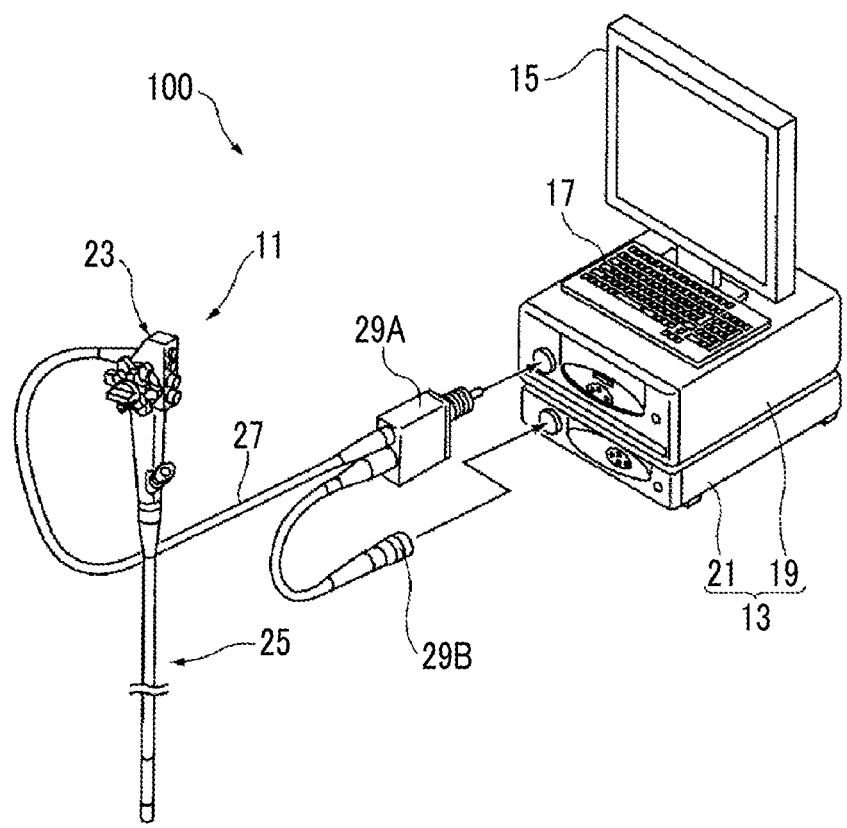
FIG. 2 is an external view showing an example of the specific configuration of the endoscope apparatus.

FIG. 1 is a diagram for explaining the embodiment of the present invention, and is a block diagram showing the schematic configuration of an endoscope apparatus. FIG. 2 is an external view showing an example of the specific configuration of the endoscope apparatus.

<Configuration of the Endoscope Apparatus>

As shown in FIGS. 1 and 2, an endoscope apparatus 100 includes an endoscope 11, a control device 13 to which the endoscope 11 is connected, a display unit 15 connected to the control device 13, such as a liquid crystal monitor, and an input unit 17 to input information to the control device 13, such as a keyboard or a mouse.

The control device 13 is configured to include a light source device 19 that generates illumination light and a processor 21 that performs signal processing on a captured image.

The endoscope 11 includes a body operation unit 23 and an insertion unit 25 that is provided continuously to the body operation unit 23 and is inserted into the body cavity.

The body operation unit 23 is connected to a universal code 27. A light guide connector 29A provided at one distal end of the universal code 27 is connected to the light source device 19, and a video connector 29B provided at the other distal end is connected to the processor 21.

An illumination window 31 and an observation window 33 are provided at the distal end of the insertion unit 25 of the endoscope 11 opposite the body operation unit 23.

The illumination window 31 emits illumination light guided through a light guide 35 toward a subject, and the observation window 33 provides an observation image to an imaging element 37.

The light source device 19 includes a light source 39 for introducing the emitted light to the light guide 35 and a light source control unit 41 that controls the amount of light emitted from the light source 39 by pulse driving.

The processor 21 includes an imaging signal processing unit 43, an endoscope control unit 45, an image processing unit 47, and a memory 49.

The endoscope 11 includes an imaging control unit 51 for controlling the driving of the imaging element 37.

The imaging control unit 51 controls the driving of the imaging element 37 according to an instruction from the endoscope control unit 45. The imaging element 37 and the imaging control unit 51 function as an imaging unit.

The imaging element 37 is a CMOS type image sensor driven by the rolling shutter method.

The imaging element 37 images reflected light from the subject of the illumination light, which is irradiated from the illumination window 31, through the observation window 33 and a lens (not shown). The imaging element 37 outputs an image signal of the captured observation image to the processor 21.

The endoscope control unit 45 is connected to the memory 49 as storage means for storing an observation image or various kinds of information, and the image signal output from the imaging signal processing unit 43 is subjected to appropriate image processing by the image processing unit 47 and is output to the display unit 15 as an image.

In addition, the endoscope control unit 45 is connected to a network such as a LAN (not shown), and controls the entire endoscope apparatus 100 (for example, delivers information including an imaging signal).

The endoscope control unit 45 functions as an imaging signal generation unit that generates an imaging signal according to illumination light to be described later.

The observation image formed and captured on the light receiving surface of the imaging element 37 is converted into an electrical signal, and the electrical signal is input to the imaging signal processing unit 43 of the processor 21. The imaging signal processing unit 43 converts the input signal of the observation image into an imaging signal.

The light source 39 includes one or more laser light sources that are semiconductor light emitting elements.

The light source 39 may be configured to emit only specific wavelength light or emit light beams of a plurality of wavelengths simultaneously in addition to generating white light. As the specific wavelength light, blue narrowband wavelength light having a narrower wavelength width than white illumination light, wavelength light for fluorescence observation, near-infrared light for infrared observation, and the like can be mentioned.

The light source that generates white light is configured to include a laser light source, which outputs blue laser light having a center wavelength of 445 nm, and a wavelength conversion member including a plurality of types of phosphors (for example, phosphors including a YAG-based phosphor or a phosphor containing BAM ($BaMgAl_{10}O_{37}$)) that absorb a part of the blue laser light and perform excitation and emission of green to yellow.

As this laser light source, for example, a broad area type InGaN-based laser diode can be used. According to the configuration described above, blue laser light from the laser light source and excitation light of green to yellow, which is obtained by wavelength conversion of the blue laser light, are combined to generate white light. The intensity of light emitted from the light source 39 is arbitrarily adjusted by pulse modulation driving.

A wavelength conversion member (not shown) is disposed in the light source 39. The white light from the wavelength conversion member is guided to the illumination window 31, which is disposed at the distal end of the endoscope insertion unit 25, through the light guide 35 formed of a fiber bundle including a large number of fibers.

The light source 39 can generate illumination light suitable for the observation of capillaries or fine patterns of the living tissue surface layer by providing, for example, a laser light source that outputs laser light having a center wavelength of 405 nm in addition to the laser light source for the white light described above.

In this case, the light source 39 may be configured to use mixed light, which is obtained by simultaneously emitting laser light having a center wavelength of 405 nm and white light based on laser light having a center wavelength of 445 nm at an arbitrary ratio, as illumination light for endoscopic observation.

The light source 39 may also be configured such that the wavelength conversion member is disposed at a position closest to the illumination window 31. In this case, it is possible to adopt a configuration in which one or more single-mode optical fibers are provided along the endoscope insertion unit 25 instead of the light guide 35 and light of the light emitting end is emitted toward the wavelength conversion member. In this case, it is possible to reduce the diameter of the endoscope insertion unit.

The light source 39 may be formed by a light emitting diode instead of the laser light source. In addition, desired wavelength light, such as red light (R light), green light (G light), blue light (B light), or blue narrowband light, may be obtained by combining color filters that extract white light and specific wavelength light selectively.

Next, how to perform frame exposure by the rolling shutter operation using the endoscope apparatus 100 having the above-described configuration will be described.

Figure 3:
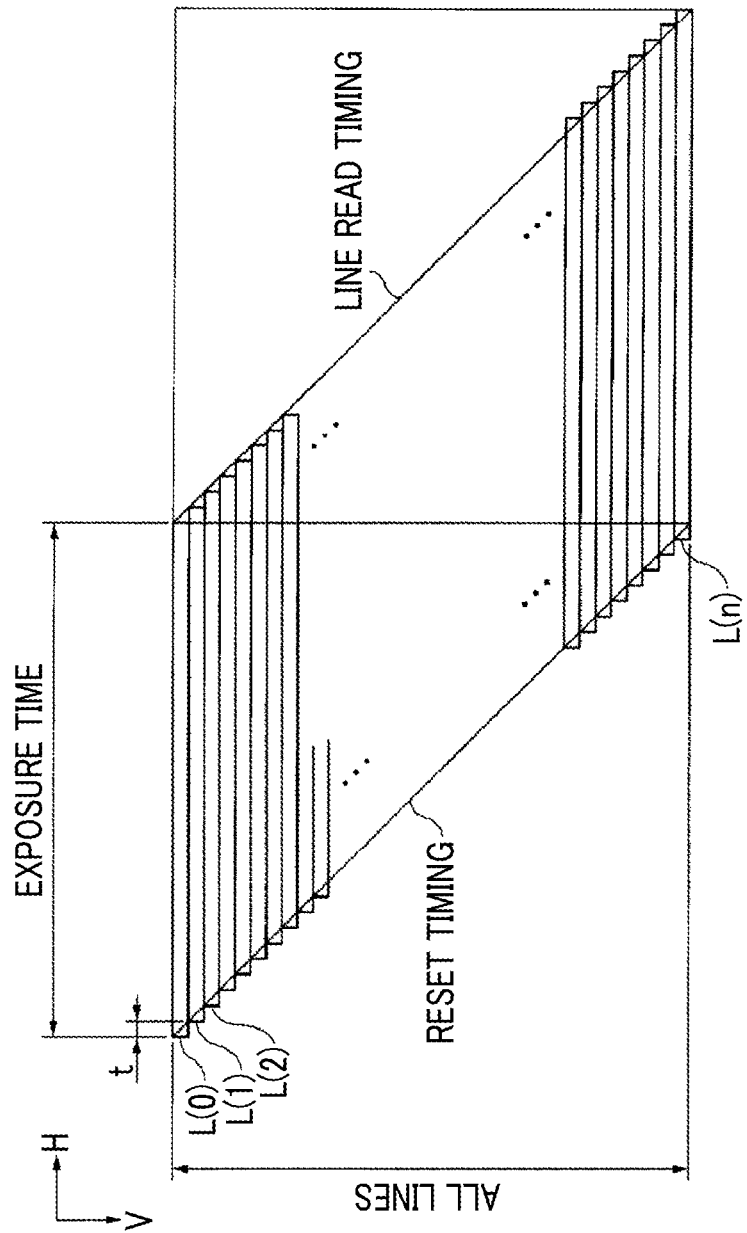
FIG. 3 is a schematic explanatory diagram showing the exposure timing of an imaging element according to a rolling shutter method.

FIG. 3 is a schematic explanatory diagram showing the exposure timing of the imaging element according to the rolling shutter method.

The rolling shutter method of this configuration example is a method in which, when respective horizontal pixel lines L(1), L(2), . . . , L(n) aligned in a horizontal direction H are sequentially scanned in a vertical direction V from the upper end line to the lower end line in a pixel area of an imaging element in which pixels formed by a number of photoelectric conversion elements are arrayed in the horizontal direction H and the vertical direction V, the exposure start timing of the respective horizontal pixel lines L(1), L(2), . . . , L(n) is set so as to be shifted in a direction, in which the exposure start timing is sequentially delayed for each horizontal pixel line, by a horizontal scanning period t sequentially from the upper end line on one end side in the vertical direction.

The amount of delay is set such that the exposure end timing of the lower end line matches the exposure start timing of the upper end line in the next frame.

The horizontal scanning period t is a time required per line, which is required for instruction on a logic circuit such as reset and accumulated charge line reading, for one line of one horizontal pixel line (hereinafter, may be simply referred to as a line), and is expressed as an exposure start time difference between the lines L(1) and L(2) shown in FIG. 3.

In addition, although there are various kinds of driving methods in the rolling shutter method, other driving methods can also be applied within a range that does not deviate from the spirit of the present invention.

Figure 4:
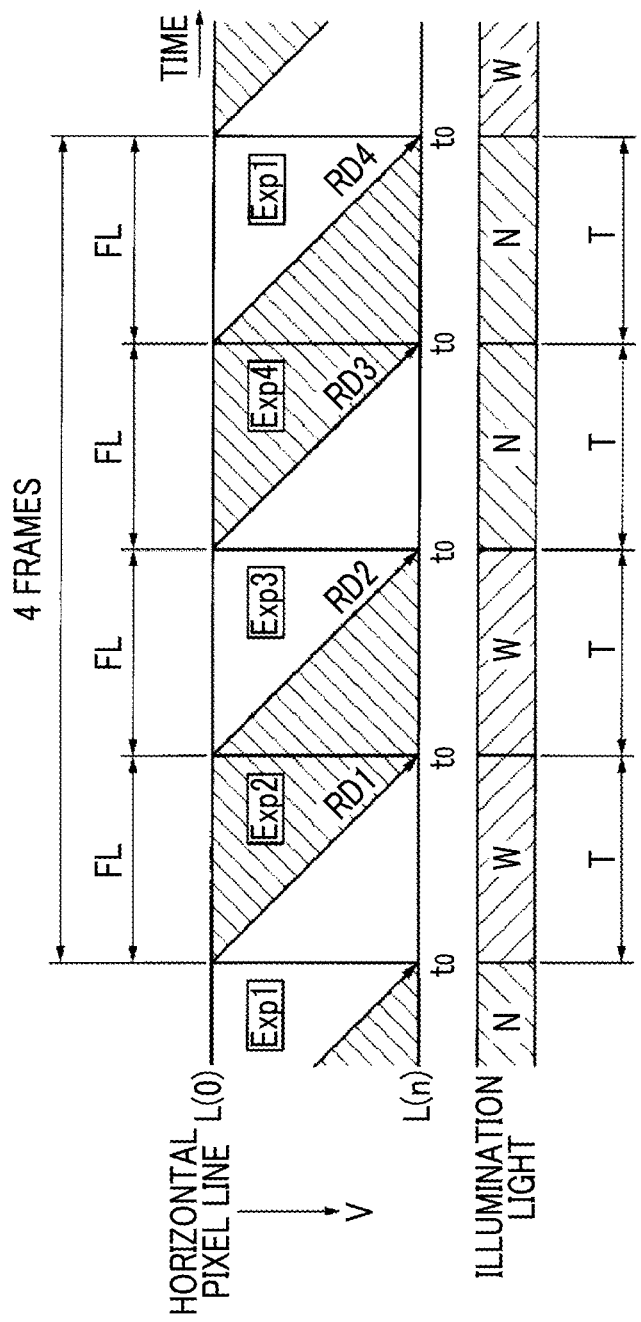
FIG. 4 is a general exposure time chart showing a state in which imaging based on the frame sequential method is performed using a rolling shutter type imaging element by alternately emitting white illumination light (W light) and illumination light (N light) having a blue narrowband wavelength.

FIG. 4 shows a general exposure time chart when performing imaging based on the frame sequential method using a rolling shutter type imaging element by alternately emitting white illumination light (W light) and illumination light (N light) having a blue narrowband wavelength.

In this case, the endoscope control unit 45 (refer to FIG. 1) emits W light or N light continuously during a two-frame period (twice one frame period FL) required to obtain an image of one frame from the imaging element 37.

The light source control unit 41 sets a unit irradiation period T every exposure start timing $t_0$ in the horizontal pixel line on the upper end side of the imaging element 37, and emits the illumination light from the light source 39 every unit irradiation period.

That is, an exposure frame Exp2 that is a next frame of an exposure frame Exp1 is a frame image exposed at the time of irradiation of W light.

In addition, an exposure frame Exp4 that is a next frame of an exposure frame Exp3 is a frame image exposed at the time of irradiation of N light.

Therefore, in order to finish the acquisition of a frame imaging signal based on W light illumination and a frame imaging signal based on N light illumination, a total of four frames are required.

Next, instead of the exposure control described above, exposure control to finish the acquisition of the frame imaging signal based on W light illumination and the frame imaging signal based on N light illumination with a total of three frames will be described.

Figure 5:
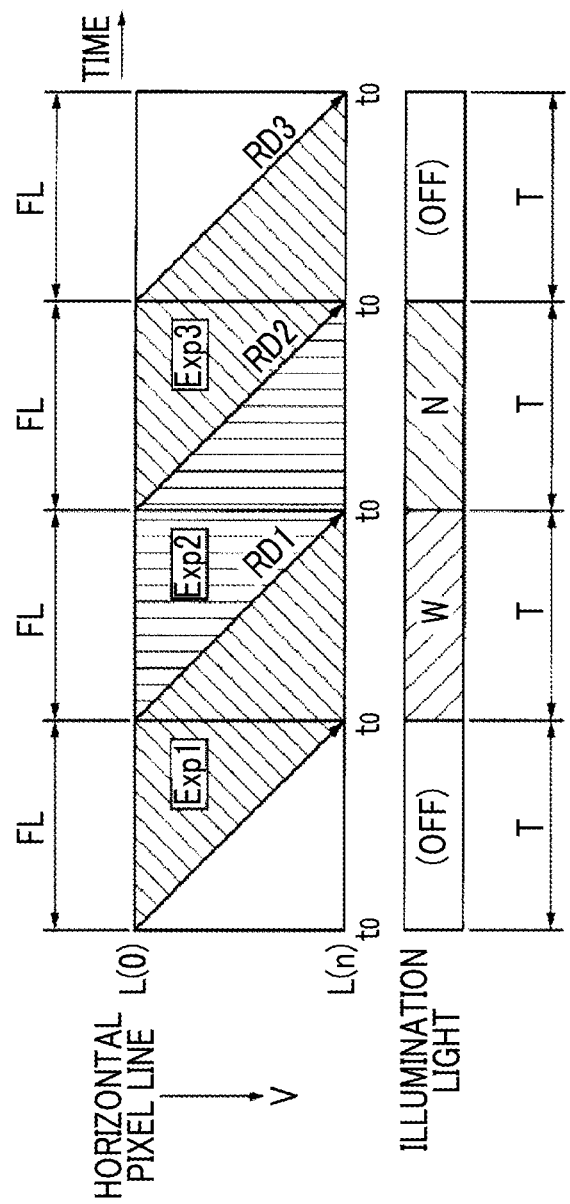
FIG. 5 is an exposure time chart showing a state in which a light source control unit performs imaging based on the frame sequential method using a rolling shutter type imaging element by alternately emitting white illumination light (W light) and illumination light (N light) having a blue narrowband wavelength while inserting a frame, in which no illumination light is irradiated, before and after the frames in which the white illumination light (W light) and the illumination light (N light) are irradiated.

FIG. 5 shows an exposure time chart when the light source control unit 41 performs imaging based on the frame sequential method using a rolling shutter type imaging element by alternately emitting the white illumination light (W light) and the illumination light (N light) having a blue narrowband wavelength while inserting a frame, in which no illumination light is irradiated, before and after the frames in which the white illumination light (W light) and the illumination light (N light) are irradiated. In addition, the exposure period of each horizontal pixel line in FIG. 5 is shown as the maximum exposure period that can be set.

The light source control unit 41 emits the W light and the N light every unit irradiation period T. In addition, the unit irradiation period T in which no illumination light is emitted is set before and after a plurality of continuous unit irradiation periods T in which the W light and the N light have been emitted.

That is, the light source control unit 41 sets "no emission of illumination light", "emission of W light", "emission of N light", and "no emission of illumination light" as one period, and controls illumination light by repeating this period.

As a result, the first exposure frame Exp1 is formed by the unit irradiation period T in which the W light is emitted and the unit irradiation period T in which no illumination light is emitted.

The second exposure frame Exp2 is formed by the unit irradiation period T in which the W light is emitted and the unit irradiation period T in which the N light is emitted.

The third exposure frame Exp3 is formed by the unit irradiation period T in which the N light is emitted and the unit irradiation period T in which no illumination light is emitted.

Figure 6:
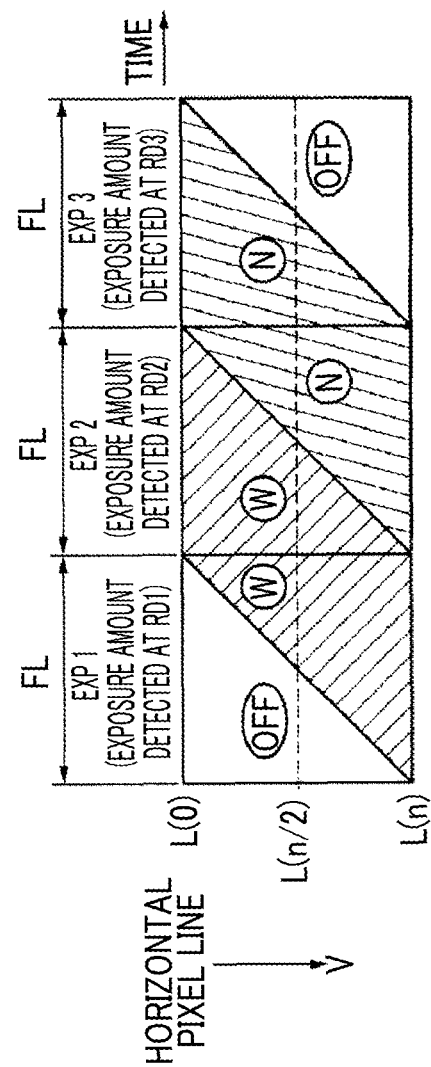
FIG. 6 is an exposure time chart showing each exposure frame shown in FIG. 5 by eliminating the shift of each horizontal pixel line equivalent to the horizontal scanning period.

FIG. 6 is an exposure time chart showing each exposure frame shown in FIG. 5 by eliminating the shift of each horizontal pixel line equivalent to the horizontal scanning period.

A shaded region in each of the exposure frames Exp1, Exp2, and Exp3 is an exposure period corresponding to either the exposure by the W light or the exposure by the N light.

The timing of switching of illumination light for each exposure frame is determined according to the shift of the horizontal pixel line equivalent to the horizontal scanning period t (refer to FIG. 3) due to the rolling shutter of the imaging element, and is uniquely determined by the imaging element and the driving control pattern of the imaging element.

In the exposure frame Exp1, a line i=0 on one end side of the horizontal pixel line of the imaging element is an exposure period in which no illumination light is emitted.

A middle line i=n/2 (n is the total number of lines) is an exposure period in which the percentage of the exposure period, in which no illumination light is emitted, and the percentage of the exposure period, in which the W light is emitted, are the same.

A line i=n on the other end side is an exposure period in which the W light is emitted continuously.

In the exposure frame Exp2, the exposure period in which the W light is irradiated and the exposure period in which the N light is irradiated are mixed. In the exposure frame Exp3, the exposure period in which the N light is irradiated and the exposure period in which no illumination light is irradiated are mixed.

Next, a procedure for generating an imaging signal, which is obtained from each pixel when all pixels are exposed by the same illumination light in the set exposure time (length of one frame FL in FIG. 5), from the exposure frames Exp1, Exp2, and Exp3 shown in FIG. 6 will be described.

Figure 7:
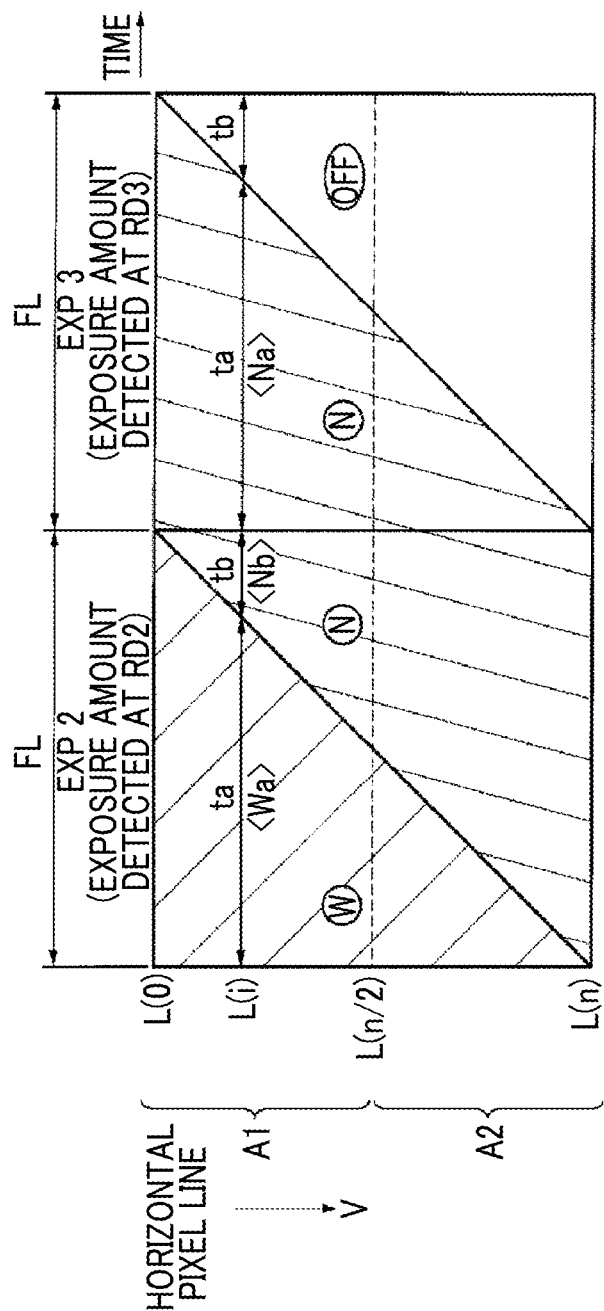
FIG. 7 is an explanatory diagram showing exposure frames Exp2 and Exp3 shown in FIG. 6 in an enlarged manner.

FIG. 7 is an explanatory diagram showing the exposure frames Exp2 and Exp3 shown in FIG. 6 in an enlarged manner.

The endoscope control unit 45 divides horizontal pixel lines into a first line group A1 on one end side (upper end side) in a direction perpendicular to all horizontal pixel lines of the imaging element 37 and a second line group A2 on the other end side (lower end side) with the middle line i=n/2 in the vertical direction as a boundary.

In the exposure frame Exp2, an arbitrary horizontal pixel line L(i) in the first line group A1 will be described as an example. In this case, the entire exposure period in the line L(i) is a sum of the exposure period ta in which the W light is emitted to expose the imaging element 37 and the exposure period tb in which the N light is emitted to expose the imaging element 37.

In the exposure period ta, in the imaging signal amount of the line L(i) (imaging signal amount read at the read timing RD2 in FIG. 5), ta/(ta+tb) is the amount of signal <Wa> by the W light, and tb/(ta+tb) is the amount of signal <Nb> by the N light.

In the exposure frame Exp3, the entire exposure period in the line L(i) is a sum of the exposure period ta in which the N light is emitted to expose the imaging element 37 and the exposure period tb in which no illumination light is emitted.

Since the exposure period tb of the exposure frame Exp3 is a period in which no illumination light is emitted, the imaging signal amount of the line L(i) (imaging signal amount read at the read timing RD3 in FIG. 5) is the amount of signal <Na> entirely by the N light.

The endoscope control unit 45 calculates an imaging signal Iw(i), which is obtained from each pixel of the line L(i) when exposure using the W light is performed for the entire exposure period of the line L(i), and an imaging signal In(i), which is obtained from each pixel of the line L(i) when exposure using the N light is performed for the entire exposure period of the line L(i).

For the imaging signal Iw(i), the endoscope control unit 45 performs the calculation using an imaging signal obtained from one of the first and second line groups A1 and A2 in which the percentage of the imaging signal amount by the W light for each horizontal pixel line is larger.

For the imaging signal In(i), the endoscope control unit 45 performs the calculation using an imaging signal obtained from one of the first and second line groups A1 and A2 in which the percentage of the imaging signal amount by the N light for each horizontal pixel line is larger.

Hereinafter, a procedure for generating an imaging signal of each pixel according to illumination light will be described.

<Imaging Signal Iw(i)|Case of $0 \leq i < (n/2)$|>

The imaging signal Iw(i) by the W light in the first line group A1 is calculated using the imaging signal of the first line group A1 of the exposure frame Exp2, in which the percentage of the amount of exposure by the W light is large, and the imaging signal of the first line group A1 of the next exposure frame Exp3.

In the exposure frame Exp2, the imaging signal amount Iw(i), which is obtained from each pixel of the horizontal pixel line L(i) when exposure using the W light is performed for the entire exposure period, is $\{(ta+tb)/ta\}$ times the imaging signal amount Wa shown in FIG. 7.

Assuming that the imaging signal amount read from each pixel of the horizontal pixel line L(i) at the read timing RD2 is RD2, the imaging signal amount Wa shown in FIG. 7 is obtained by subtracting the imaging signal amount Nb in FIG. 7 from RD2.

The imaging signal amount Nb shown in FIG. 7 is calculated by the operation of Na×(tb/ta). Here, Na matches the imaging signal amount read from each pixel of the horizontal pixel line L(i) at the read timing RD3.

Therefore, assuming that the imaging signal amount read from each pixel of the horizontal pixel line L(i) at the read timing RD3 is RD3, Nb shown in FIG. 7 is expressed as Nb=RD3×(tb/ta).

From the above, the imaging signal amount Iw(i), which is obtained from each pixel of the horizontal pixel line L(i) when exposure using the W light is performed for the entire exposure period, is calculated by the following Expression (1) in the range of $0 \leq i < (n/2)$.

$$Iw(i) = Wa \times \frac{ta+tb}{tb} = (RD2 - Nb) \times \frac{ta+tb}{tb} \qquad (1)$$
$$= \left(RD2 - RD3 \times \frac{tb}{ta}\right) \times \frac{ta+tb}{tb}$$

The endoscope control unit 45 generates the imaging signal Iw(i) corresponding to each horizontal pixel line of the horizontal pixel lines L(0) to L(n/2) by calculating the above-described Iw(i) for each pixel on each horizontal pixel line L(i) (i=0 to n/2).

<Imaging Signal Iw(i)|Case of (2/n)≤i≤n|>

The imaging signal Iw(i) by the W light in the second line group A2 is calculated using the imaging signal of the second line group A2 of the exposure frame Exp1, in which the percentage of the amount of exposure by the W light is large, and the imaging signal of the second line group A2 of the next exposure frame Exp2.

Figure 8:
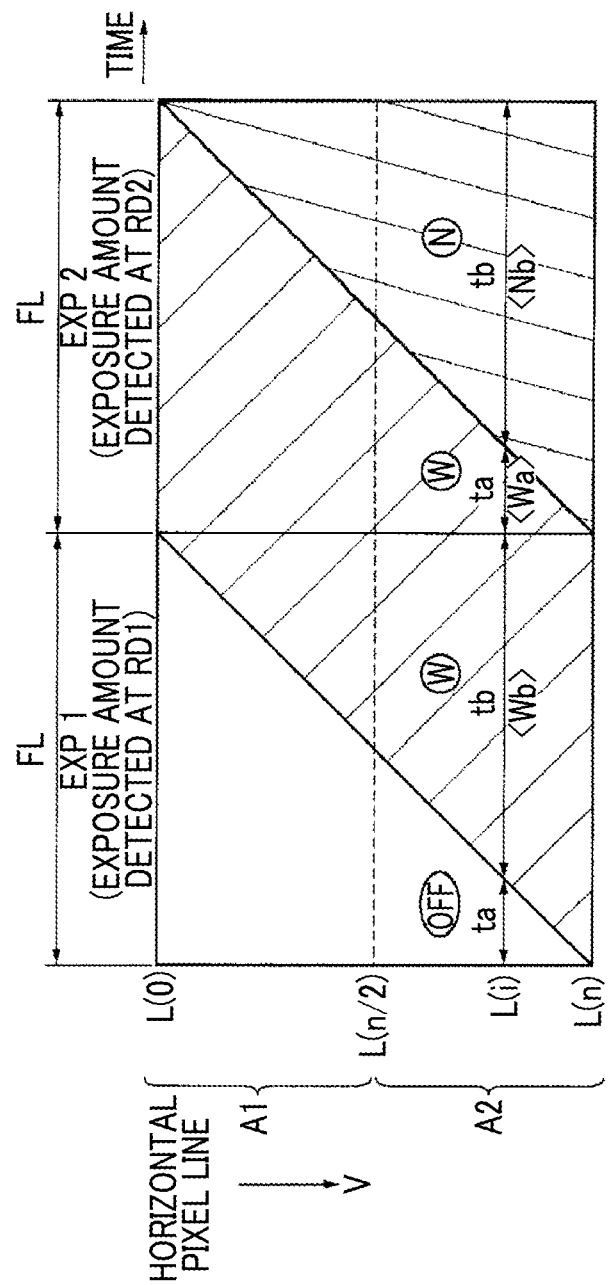
FIG. 8 is an explanatory diagram showing exposure frames Exp1 and Exp2 shown in FIG. 6 in an enlarged manner.

FIG. 8 is an explanatory diagram showing the exposure frames Exp1 and Exp2 shown in FIG. 6 in an enlarged manner.

In the exposure frame Exp1, an arbitrary horizontal pixel line L(i) in the second line group A2 will be described as an example. In this case, the entire exposure period in the line L(i) is a sum of the exposure period ta in which no illumination light is emitted and the exposure period tb in which the W light is emitted to expose the imaging element 37.

Since the exposure period ta of the exposure frame Exp1 is a period in which no illumination light is emitted, the imaging signal amount of the line L(i) (imaging signal amount read at the read timing RD1 in FIG. 5) is the amount of signal <Wb> entirely by the W light.

Therefore, assuming that the imaging signal read from each pixel of the horizontal pixel line L(i) at the read timing RD1 is RD1, the imaging signal Iw(i) in the second line group A2 is expressed by Expression (2) in the range of (2/n)≤i≤n.

$$Iw(i) = RD1 \times \frac{ta+tb}{tb} \quad (2)$$

In addition, the middle line i=n/2 may be treated as one middle line if the total number of lines n is an odd number and may be treated as two middle lines if the total number of lines n is an even number.

The endoscope control unit 45 generates the imaging signal Iw(i) corresponding to each horizontal pixel line of the horizontal pixel lines L(0) to L(n) using Expressions (1) and (2) described above.

<Imaging Signal In(i) for N Light|Case of 0≤i<(n/2)|>

The imaging signal In(i) by the N light in the first line group A1 is calculated from the imaging signal of the first line group A1 of the exposure frame Exp3 in which the percentage of the amount of exposure by the N light is large. The imaging signal In(i) is expressed by Expression (3) in the range of 0≤i<(n/2).

$$In(i) = RD3 \times \frac{ta+tb}{ta} \quad (3)$$

The endoscope control unit 45 generates the imaging signal In(i) corresponding to each horizontal pixel line of the horizontal pixel lines L(1) to L(n/2) by calculating the above-described In(i) for each pixel on each horizontal pixel line L(i) (i=0 to n/2).

<Imaging Signal In(i) for N Light|Case of (2/n)≤i≤n|>

The imaging signal In(i) by the N light in the second line group A2 is calculated from the imaging signal of the second line group A2 of the exposure frame Exp2 in which the percentage of the amount of exposure by the N light is large. The imaging signal In(i) is expressed by Expression (4) in the range of (2/n)≤i≤n.

$$In(i) = Nb \times \frac{ta+tb}{tb} = (RD2 - Wa) \times \frac{ta+tb}{tb} \quad (4)$$
$$= \left(RD2 - RD1 \times \frac{ta}{tb}\right) \times \frac{ta+tb}{tb}$$

The endoscope control unit 45 generates the imaging signal In(i) corresponding to each horizontal pixel line of the horizontal pixel lines L(0) to L(n) using Expressions (3) and (4) described above.

The information of each expression described above is stored in the memory 49 in advance, and the endoscope control unit 45 calculates the imaging signals Iw(i) and In(i) by substituting RD1 to RD3, which are actually obtained, into each expression.

The calculated imaging signals Iw(i) and In(i) are output to the image processing unit 47. The image processing unit 47 generates captured image data by image processing using each imaging signal, and outputs the image data to the display unit 15. Each imaging signal may be stored in a storage medium or the like (not shown).

As described above, from three frames of the exposure frames Exp1, Exp2, and Exp3 shown in FIG. 6, the imaging signal amount of each pixel when exposed by the same illumination light is calculated for each horizontal pixel line based on the first period to from the exposure start timing of each horizontal pixel line to the switching timing of illumination light and the second period tb from the switching timing of illumination light to the exposure end timing.

Thus, the imaging signal Iw(i) by the W light and the imaging signal In(i) by the N light can be separately generated. According to this exposure control, since one frame is reduced from four frames required in the case of general exposure control, it is possible to improve video responsiveness. In addition, it is possible to suppress the occurrence of color shift on the captured image.

Figure 9:
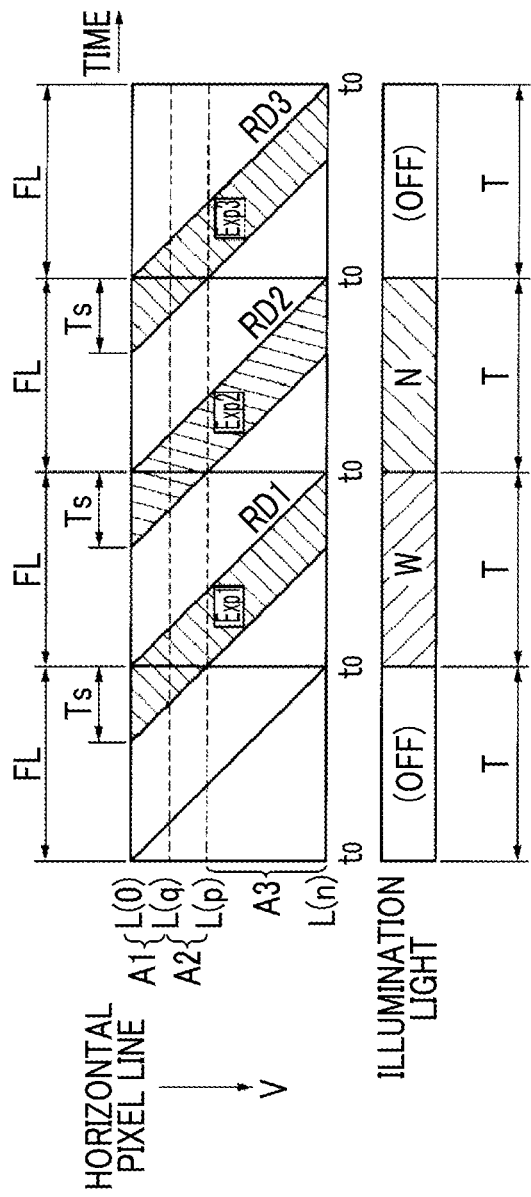
FIG. 9 is an exposure time chart in which the exposure period of each horizontal pixel line is a back-stuffed exposure period Ts that is shorter than the maximum exposure period.

As shown in FIG. 9, when the exposure period of each horizontal pixel line is a back-stuffed exposure period Ts that is shorter than the maximum exposure period, the endoscope control unit 45 divides lines as follows instead of the above-described division of the line groups A1 and A2.

That is, the endoscope control unit 45 sets a line, which bisects a horizontal pixel line group in the vertical direction, as a middle line (line of i=q), the horizontal pixel line group including a horizontal pixel line (line of i=0) on one end side of the imaging element 37 in the vertical direction to a horizontal scanning line (line of i=p) having the exposure start timing that matches the exposure end timing of the horizontal pixel line.

With this middle line as a boundary, the horizontal pixel line group is divided into the first line group A1 on one end side (upper end side) in the vertical direction and the second line group A2 on the other end side (lower end side).

The endoscope control unit 45 calculates imaging signals for the first and second line groups A1 and A2 for specific illumination light.

For the third line group A3 including horizontal pixel lines closer to the other end side than the second line group A2 is, imaging signals read from the third line group A3 are used as they are since there is no mixture of illumination light in the exposure period.

Next, an example of exposure control in which types of illumination light are R light, G light, and B light will be described.

Figure 10:
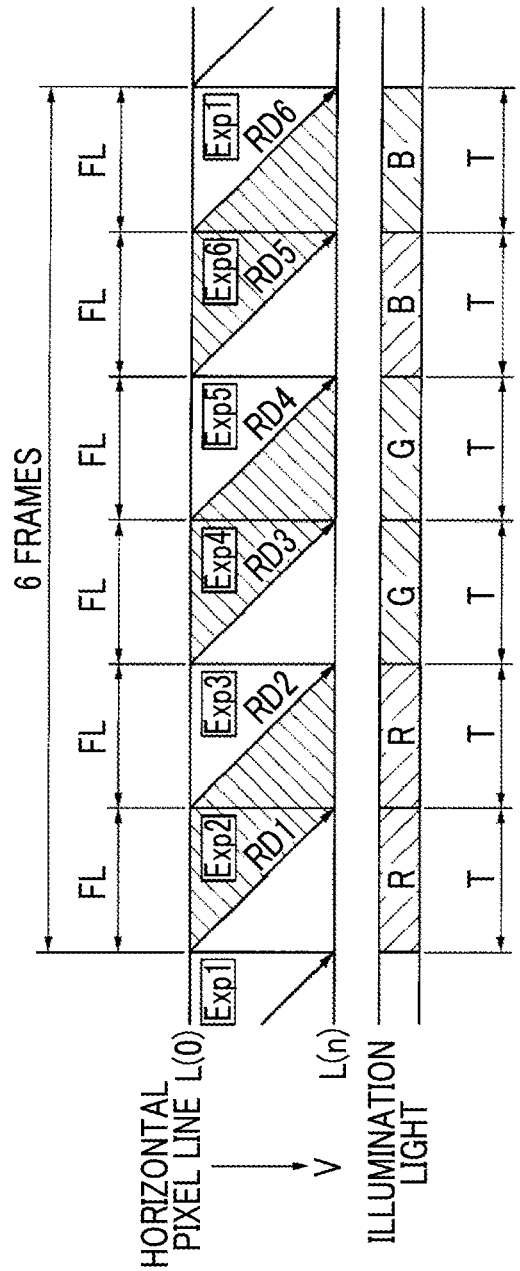
FIG. 10 is a general exposure time chart showing a state in which imaging based on the frame sequential method is performed using a rolling shutter type imaging element by alternately emitting R light, G light, and B light.

FIG. 10 shows a general exposure time chart when performing imaging based on the frame sequential method using a rolling shutter type imaging element by alternately emitting R light, G light, and B light.

In this case, the endoscope control unit 45 (refer to FIG. 1) emits R light, G light, and B light continuously in each period of a two-frame period required to obtain an image of one frame from the imaging element 37.

That is, the exposure frame Exp2 that is a next frame of the exposure frame Exp1 is a frame image exposed at the time of irradiation of R light. In addition, the exposure frame Exp4 that is a next frame of the exposure frame Exp3 is a frame image exposed at the time of irradiation of G light. In addition, the exposure frame Exp6 that is a next frame of the exposure frame Exp5 is a frame image exposed at the time of irradiation of B light.

Therefore, in order to finish the acquisition of a frame imaging signal based on R light illumination, a frame imaging signal based on G light illumination, and a frame imaging signal based on B light illumination, a total of six frames are required.

Next, instead of the exposure control described above, exposure control to finish the acquisition of the frame imaging signal based on R light illumination, the frame imaging signal based on G light illumination, and the frame imaging signal based on B light illumination with a total of four frames will be described.

Figure 11:
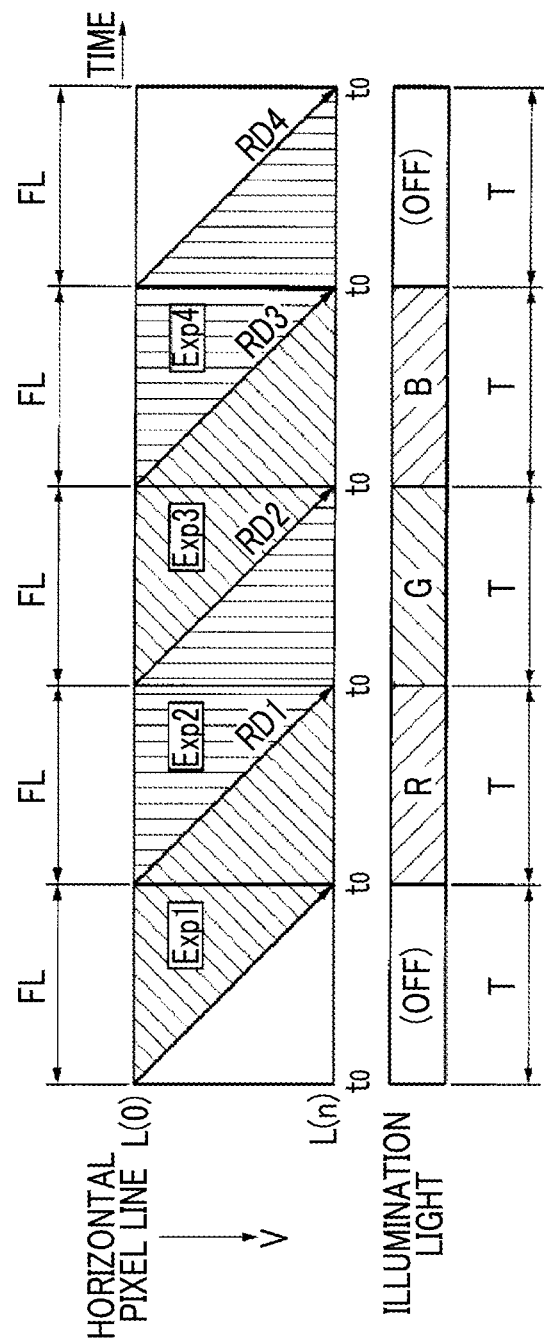
FIG. 11 is an exposure time chart when a light source control unit performs imaging based on the frame sequential method using a rolling shutter type imaging element by alternately emitting white illumination light (W light) and illumination light (N light) having a blue narrowband wavelength while inserting a frame, in which no illumination light is irradiated, before and after the frames in which the white illumination light (W light) and the illumination light (N light) are irradiated.

FIG. 11 shows an exposure time chart when the light source control unit 41 performs imaging based on the frame sequential method using a rolling shutter type imaging element by continuously emitting R light, G light, and B light while inserting a frame, in which no illumination light is irradiated, before and after the frames in the R light, the G light, and the B light are irradiated.

The light source control unit 41 emits R light, G light, and B light every unit irradiation period T, and sets the unit irradiation period T, in which no illumination light is emitted, before and after a plurality of continuous unit irradiation periods T in which the R light, the G light, and the B light are emitted, respectively.

That is, the light source control unit 41 sets "no emission of illumination light", "emission of R light", "emission of G light", "emission of B light", and "no emission of illumination light" as one period, and controls illumination light by repeating this period.

The first exposure frame Exp1 is formed by the unit irradiation period T in which the R light is emitted and the unit irradiation period T in which no illumination light is emitted.

The second exposure frame Exp2 is formed by the unit irradiation period T in which the R light is emitted and the unit irradiation period T in which the G light is emitted.

The third exposure frame Exp3 is formed by the unit irradiation period T in which the G light is emitted and the unit irradiation period T in which the B light is emitted.

The fourth exposure frame Exp4 is formed by the unit irradiation period T in which the B light is emitted and the unit irradiation period T in which no illumination light is emitted.

Figure 12:
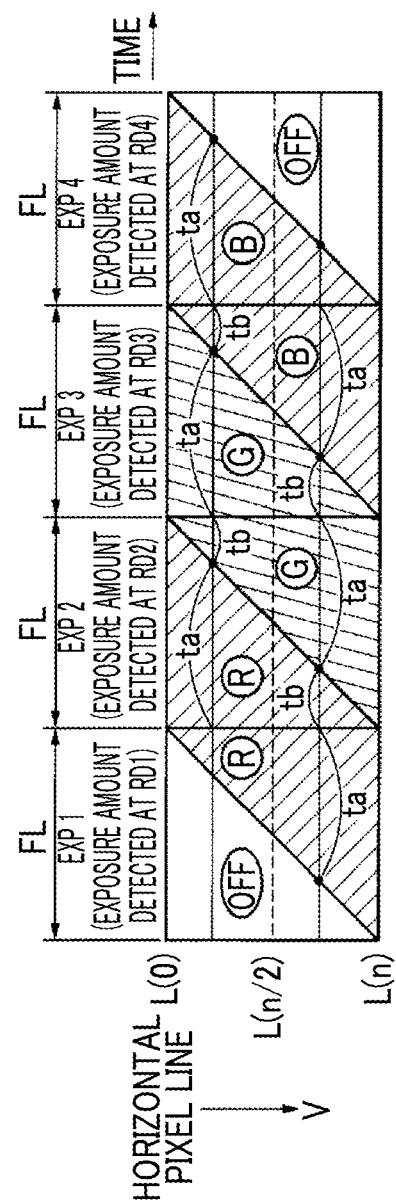
FIG. 12 is an exposure time chart showing each exposure frame shown in FIG. 11 by eliminating the shift of each horizontal pixel line equivalent to the horizontal scanning period.

FIG. 12 is an exposure time chart showing each exposure frame shown in FIG. 11 by eliminating the shift of each horizontal pixel line equivalent to the horizontal scanning period. A shaded region in each of the exposure frames Exp1, Exp2, Exp3, and Exp4 is an exposure period corresponding to one of the exposure by R light, the exposure by G light, and the exposure by B light.

The timing of switching of illumination light for each exposure frame is determined according to the shift of the horizontal pixel line equivalent to the horizontal scanning period t (refer to FIG. 3) due to the rolling shutter of the imaging element, and is uniquely determined by the imaging element and the driving control pattern of the imaging element.

Hereinafter, a procedure for generating an imaging signal of each pixel according to illumination light will be described.

In the same manner as in the above-described case of illumination light of the W light and the N light, an imaging signal Ir(i) by R light can be calculated by Expression (5) in the range of $0 \leq i < (n/2)$ and by Expression (6) in the range of $(2/n) \leq i \leq n$ with the imaging signal amount, which is read at the read timing RD2, RD3, and RD4 in FIG. 11, as RD2, RD3, and RD4.

$$Ir(i) = \left\{ RD2 - \frac{tb}{ta}\left(RD3 - RD4 \times \frac{tb}{ta}\right)\right\} \times \frac{ta+tb}{tb} \quad (5)$$

$$Ir(i) = RD1 \times \frac{ta+tb}{tb} \quad (6)$$

In the same manner as described above, an imaging signal Ib(i) by B light can be calculated by Expression (7) in the range of $0 \leq i < (n/2)$ and by Expression (8) in the range of $(2/n) \leq i \leq n$ with the imaging signal amount, which is read at the read timing RD1 in FIG. 11, as RD1

$$Ib(i) = RD4 \times \frac{ta+tb}{ta} \quad (7)$$

$$Ib(i) = \left\{ RD3 - \frac{tb}{ta}\left(RD2 - RD1 \times \frac{tb}{ta}\right)\right\} \times \frac{ta+tb}{ta} \quad (8)$$

An imaging signal Ig(i) by G light is calculated as follows.

Figure 13:
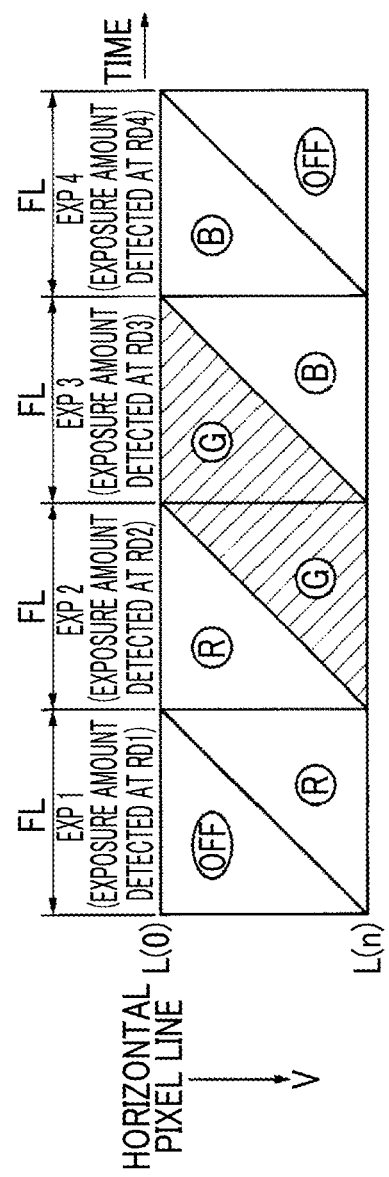
FIG. 13 is an exposure time chart showing each exposure frame shown in FIG. 11 by eliminating the shift of each horizontal pixel line equivalent to the horizontal scanning period.

As FIG. 13 schematically shows each exposure frame, a sum of RD2 and RD3 in each horizontal pixel line of the exposure frames Exp2 and Exp3 includes the imaging signal amount by R light and the imaging signal amount by B light as well as the imaging signal amount by G light.

Therefore, the imaging signal amount by only the G light can be calculated by subtracting the imaging signal amount by R light in the exposure frame Exp1 and the imaging signal amount by G light in the exposure frame Exp4 from the sum of RD2 and RD3. Accordingly, the imaging signal amount by G light is calculated from Expression (9) in the full range of i=0 to n using the exposure frames Exp1, Exp2, Exp3, and Exp4.

$$Ig(i) = RD2 + RD3 - RD1 - RD4 \quad (9)$$

As described above, the imaging signal Ir(i) by R light, the imaging signal Ig(i) by G light, and the imaging signal Ib(i) by B light can be generated from four frames of the exposure frames Exp1, Exp2, Exp3, and Exp4 shown in FIG. 11.

As described above, even if imaging based on the frame sequential method is performed using a rolling shutter type imaging element by sequentially switching a plurality of types of illumination light beams, it is possible to perform imaging by switching the respective illumination light beams at a high speed. As a result, it is possible to improve video responsiveness.

In addition, according to the method described above, it is possible to generate an imaging signal according to illumination light, which is excellent in color reproducibility, since there is no occurrence of color mixture. Therefore, it is possible to perform imaging based on the frame sequential method that is comparable to the global shutter type imaging element.

Next, another example of the method of generating an imaging signal according to illumination light of W light and N light will be described.

<Imaging Signal In(i)|Case of 0≤i<(n/2)|>

The imaging signal In(i) by the N light in the first line group A1 is calculated by the following Expression (10) using the imaging signal amount RD3 of the first line group A1 of the exposure frame Exp3 in which the percentage of the amount of exposure by the N light is large.

$$In(i) = RD3 \times \frac{n}{n-i} \quad (10)$$

<Imaging Signal Iw(i)|Case of 0≤i<(n/2)|>

The imaging signal Iw(i) by the W light in the first line group A1 is calculated using the imaging signal amount RD2 of the first line group A1 of the exposure frame Exp2, in which the percentage of the amount of exposure by the W light is large, and In(i) calculated by Expression (10).

RD2 is expressed by the following Expression (11) using Iw(i) and In(i).

$$RD2 = \frac{n-i}{n} \times Iw(i) + \frac{i}{n} \times In(i) \quad (11)$$

Expression (12) is obtained by transforming Expression (11).

$$Iw(i) = \frac{n}{n-i}\left(RD2 - \frac{i}{n} \times In(i)\right) \quad (12)$$

Expression (13) is obtained by substituting Expression (10) into Expression (12).

$$Iw(i) = \frac{n}{n-i}\left(RD2 - \frac{i}{n-i} \times RD3\right) \quad (13)$$

From Expression (13), it is possible to calculate the imaging signal Iw(i) by the W light in the first line group A1.

<Imaging Signal Iw(i)|Case of (2/n)≤i≤n|>

The imaging signal Iw(i) by the W light in the second line group A2 is calculated by the following Expression (14) using the imaging signal amount RD1 of the second line group A2 of the exposure frame Exp1 in which the percentage of the amount of exposure by the W light is large.

$$Iw(i) = RD1 \times \frac{n}{i} \quad (14)$$

<Imaging Signal In(i)|Case of (2/n)≤i≤n|>

The imaging signal In(i) by the N light in the second line group A2 is calculated using the imaging signal amount RD2 of the second line group A2 of the exposure frame Exp2, in which the percentage of the amount of exposure by the N light is large, and Iw(i) calculated by Expression (14).

The following Expression (15) is obtained by substituting Expression (14) into Expression (12) described above and transforming the obtained expression.

$$In(i) = \frac{n}{i}\left(RD2 - \frac{n-i}{i} \times RD1\right) \quad (15)$$

From Expression (15), it is possible to calculate the imaging signal In(i) by the N light in the second line group A2.

Next, another example of the method of generating an imaging signal according to illumination light of R light, G light, and B light will be described.

<Imaging Signal Ib(i)|Case of 0≤i<(n/2)|>

The imaging signal Ib(i) by the B light in the first line group A1 is calculated by the following Expression (16) using the imaging signal amount RD4 of the first line group A1 of the exposure frame Exp4 in which the percentage of the amount of exposure by the B light is large.

$$Ib(i) = RD4 \times \frac{n}{n-i} \quad (16)$$

<Imaging Signal Ig(i)|Case of 0≤i<(n/2)|>

The imaging signal Ig(i) by the G light in the first line group A1 is calculated using the imaging signal amount RD3 of the first line group A1 of the exposure frame Exp3, in which the percentage of the amount of exposure by the G light is large, and Ib(i) calculated by Expression (16).

RD3 is expressed by the following Expression (17) using Iw(i) and In(i).

$$RD3 = \frac{n-i}{n} \times Ig(i) + \frac{i}{n} \times Ib(i) \quad (17)$$

Expression (18) is obtained by transforming Expression (17).

$$Ig(i) = \left(RD3 - \frac{i}{n} \times Ib(i)\right) \times \frac{n}{n-i} \quad (18)$$

Expression (19) is obtained by substituting Expression (16) into Expression (18).

$$Ig(i) = \frac{n}{n-i}\left(RD3 - \frac{i}{n-i} \times RD4\right) \quad (19)$$

From Expression (19), it is possible to calculate the imaging signal Ig(i) by the G light in the first line group A1.

<Imaging Signal Ir(i)|Case of 0≤i<(n/2)|>

The imaging signal Ir(i) by the R light in the first line group A1 is calculated using the imaging signal amount RD2 of the first line group A1 of the exposure frame Exp2, in which the percentage of the amount of exposure by the R light is large, and Ig(i) calculated by Expression (19).

RD2 is expressed by the following Expression (20) using Ir(i) and Ig(i).

$$RD2 = \frac{n-i}{n} \times Ir(i) + \frac{i}{n} \times Ig(i) \quad (20)$$

Expression (21) is obtained by transforming Expression (20).

$$Ir(i) = \left(RD2 - \frac{i}{n} \times Ig(i)\right) \times \frac{n}{n-i} \qquad (21)$$

Expression (22) is obtained by substituting Expression (19) into Expression (21).

$$Ir(i) = \frac{n}{n-i}\left(RD2 - \frac{i}{n-i}\left(RD3 - \frac{i}{n-i} \times RD4\right)\right) \qquad (22)$$

From Expression (22), it is possible to calculate the imaging signal Ir(i) by the R light in the first line group A1.

<Imaging Signal Ir(i)|Case of (2/n)≤i≤n|>

The imaging signal Ir(i) by the R light in the second line group A2 is calculated by the following Expression (23) using the imaging signal amount RD1 of the second line group A2 of the exposure frame Exp1 in which the percentage of the amount of exposure by the R light is large.

$$Ir(i) = RD1 \times \frac{n}{i} \qquad (23)$$

<Imaging Signal Ig(i)|Case of (2/n)≤i≤n|>

The imaging signal Ig(i) by the G light in the second line group A2 is calculated by the following Expression (24) in the same manner as described above using the imaging signal amount RD2 of the second line group A2 of the exposure frame Exp2, in which the percentage of the amount of exposure by the G light is large, and Ir(i) calculated by Expression (23).

$$Ig(i) = \frac{n}{i}\left(RD2 - \frac{n-i}{i} \times RD1\right) \qquad (24)$$

<Imaging Signal Ib(i)|Case of (2/n)≤i≤n|>

The imaging signal Ib(i) by the B light in the second line group A2 is calculated by the following Expression (25) in the same manner as described above using the imaging signal amount RD3 of the second line group A2 of the exposure frame Exp3, in which the percentage of the amount of exposure by the B light is large, and Ig(i) calculated by Expression (24).

$$Ib(i) = \frac{n}{i}\left(RD2 - \frac{n-i}{n}\left(RD2 - \frac{n-i}{i} \times RD1\right)\right) \qquad (25)$$

As described above, also by the operation using a coefficient (n/i, i/(n−i), n/(n−i), and (n−i)/n, (n−i)/i) determined by the position of the horizontal pixel line in the vertical direction and the imaging signal amounts RD1 to RD4, it is possible to calculate the imaging signal amount with reduced error.

The present invention is not limited to the embodiment described above, and the respective components of the embodiment may be combined with each other or changes and applications of the present invention may be made by those skilled in the art based on the description of this specification and known techniques. These are also included in the range of the request for protection.

For example, the imaging element of this configuration is not limited to the CMOS type image sensor, and it is possible to use any imaging element that works in the rolling shutter method.

In addition, although the horizontal pixel lines are divided into the first and second line groups A1 and A2 with the middle line i=n/2 in a direction perpendicular to all horizontal pixel lines of the imaging element 37 as a boundary in the above explanation, the boundary of the first and second line groups A1 and A2 can be set to any position without being limited to the above.

As described above, the following is disclosed in this specification.

An imaging device disclosed includes: a light source capable of emitting a plurality of types of illumination light beams having different spectra; an imaging unit including an imaging element in which a plurality of pixels are arrayed in a horizontal direction and a vertical direction and which includes a plurality of horizontal pixel lines formed by pixels arrayed in the horizontal direction and is driven by a rolling shutter method; a light source control unit that performs switching between the illumination light beams emitted from the light source; a frame image control unit that generates a first exposure frame, which is formed by a unit irradiation period in which one of the illumination light beams is emitted and a unit irradiation period in which different illumination light from the illumination light beam is emitted, and a second exposure frame, which is formed by a unit irradiation period in which one of the illumination light beams is emitted and a unit irradiation period in which no illumination light is emitted, and outputs a frame group, in which the second exposure frame is set before and after the one first exposure frame or the two continuous first exposure frames, as one period; and an imaging signal generation unit that generates an imaging signal amount, which is obtained from the pixels when the pixels are exposed using the same illumination light in the unit irradiation period, using a detection signal amount read from the pixels of each of the horizontal pixel lines in each exposure frame included in the frame group.

The imaging signal generation unit of the imaging device disclosed generates, for a horizontal pixel line where the illumination light is switched within an exposure period of each horizontal pixel line of the first and second exposure frames, the imaging signal amount of pixels of the horizontal pixel line using a ratio of a first period from an exposure start timing of the horizontal pixel line to a switching timing of the illumination light and a second period from the switching timing of the illumination light to an exposure end timing of the horizontal pixel line.

The imaging signal generation unit of the imaging device disclosed generates the imaging signal amount of pixels of the horizontal pixel line using a coefficient determined by a position of the horizontal pixel line in a vertical direction.

When performing scan driving sequentially from one end side of the horizontal pixel line in a vertical direction to the other end side, the imaging unit of the imaging device disclosed performs driving by shifting an exposure start timing of each horizontal pixel line so that an exposure end timing of the horizontal pixel line on the other end side matches an exposure start timing of the horizontal pixel line on the one end side in a next frame.

The imaging signal generation unit of the imaging device disclosed sets a line bisecting a horizontal pixel line group, which includes a horizontal pixel line on the one end side in the vertical direction to a horizontal scanning line of an exposure start timing that matches an exposure end timing of the horizontal pixel line, in the vertical direction as a division line, divides this horizontal pixel line group into a first line group on the one end side in the vertical direction and a second line group on the other end side with the division line as a boundary, and generates the imaging signal amount by changing the detection signal amount used in the pixel present in the first line group and the detection signal amount used in the pixel present in the second line group.

In the imaging device disclosed, for a horizontal pixel line where the illumination light is switched within an exposure period of each horizontal pixel line of the first and second exposure frames, a first period from an exposure start timing of the horizontal pixel line to a switching timing of the illumination light and a second period from the switching timing of the illumination light to an exposure end timing of the horizontal pixel line are determined according to a shift of the exposure start timing with respect to the horizontal pixel line of the rolling shutter.

The plurality of types of illumination light beams in the imaging device disclosed include white illumination light and narrowband wavelength light having a narrower waveguide width than the white illumination light.

The plurality of types of illumination light beams in the imaging device disclosed include at least red light, green light, and blue light.

The light source of the imaging device disclosed includes a semiconductor light emitting element.

The endoscope apparatus disclosed includes the imaging device.

What is claimed is:

1. An endoscope apparatus, comprising:
   an imaging device, comprising:
     a light source capable of emitting a plurality of types of illumination light beams having different spectra;
     an imaging unit including an imaging element in which a plurality of pixels are arrayed in a horizontal direction and a vertical direction and which includes a plurality of horizontal pixel lines formed by pixels arrayed in the horizontal direction and is driven by a rolling shutter method;
     a light source control unit that performs switching between the illumination light beams emitted from the light source;
     a frame image control unit that generates a first exposure frame, which is formed by a unit irradiation period in which one of the illumination light beams is emitted and a unit irradiation period in which a different illumination light beam having a different spectra is emitted consecutively, and a second exposure frame, which is formed by a unit irradiation period in which one of the illumination light beams is emitted and a unit irradiation period in which no illumination light is emitted, and outputs a frame group, in which the second exposure frame is set before and after the one first exposure frame or the two continuous first exposure frames, as one period; and
     an imaging signal generation unit that generates by calculating an imaging signal amount, which is equal to the imaging signal amount of the pixels in a case where the pixels are exposed using the same illumination light in the unit irradiation period, using a detection signal amount read from the pixels of each of the horizontal pixel lines in a plurality of exposure frames included in the frame group,
   wherein the imaging signal amount is generated by calculating on a horizontal pixel line basis with one imaging frame.

2. The endoscope apparatus according to claim 1, wherein the imaging signal generation unit generates, for a horizontal pixel line where the illumination light is switched within an exposure period of each horizontal pixel line of the first and second exposure frames, the imaging signal amount of pixels of the horizontal pixel line using a ratio of a first period from an exposure start timing of the horizontal pixel line to a switching timing of the illumination light and a second period from the switching timing of the illumination light to an exposure end timing of the horizontal pixel line.

3. The endoscope apparatus according to claim 2, wherein, when performing scan driving sequentially from one end side of the horizontal pixel line in a vertical direction to the other end side, the imaging unit performs driving by shifting an exposure start timing of each horizontal pixel line so that an exposure end timing of the horizontal pixel line on the other end side matches an exposure start timing of the horizontal pixel line on the one end side in a next frame.

4. The endoscope apparatus according to claim 3, wherein the imaging signal generation unit sets a line bisecting a horizontal pixel line group, which includes a horizontal pixel line on the one end side in the vertical direction to a horizontal pixel line of an exposure start timing that matches an exposure end timing of the horizontal pixel line, in the vertical direction as a division line, divides this horizontal pixel line group into a first line group on the one end side in the vertical direction and a second line group on the other end side with the division line as a boundary, and generates the imaging signal amount by changing the detection signal amount used in the pixel present in the first line group and the detection signal amount used in the pixel present in the second line group.

5. The endoscope apparatus according to claim 2, wherein, for a horizontal pixel line where the illumination light is switched within an exposure period of each horizontal pixel line of the first and second exposure frames, a first period from an exposure start timing of the horizontal pixel line to a switching timing of the illumination light and a second period from the switching timing of the illumination light to an exposure end timing of the horizontal pixel line are determined according to a shift of the exposure start timing with respect to the horizontal pixel line of the rolling shutter.

6. The endoscope apparatus according to claim 2, wherein the plurality of types of illumination light beams include white illumination light and narrowband wavelength light having a narrower waveguide width than the white illumination light.

7. The endoscope apparatus according to claim 2, wherein the plurality of types of illumination light beams include at least red light, green light, and blue light.

8. The endoscope apparatus according to claim 1, wherein the imaging signal generation unit generates the imaging signal amount of pixels of the horizontal pixel line using a coefficient determined by a position of the horizontal pixel line in a vertical direction.

9. The endoscope apparatus according to claim 8, wherein, when performing scan driving sequentially from one end side of the horizontal pixel line in a vertical direction to the other end side, the imaging unit performs driving by shifting an exposure start timing of each horizontal pixel line so that an exposure end timing of the horizontal pixel line on the other end side matches an exposure start timing of the horizontal pixel line on the one end side in a next frame.

10. The endoscope apparatus according to claim 9, wherein the imaging signal generation unit sets a line bisecting a horizontal pixel line group, which includes a horizontal pixel line on the one end side in the vertical direction to a horizontal pixel line of an exposure start timing that matches an exposure end timing of the horizontal pixel line, in the vertical direction as a division line, divides this horizontal pixel line group into a first line group on the one end side in the vertical direction and a second line group on the other end side with the division line as a boundary, and generates the imaging signal amount by changing the detection signal amount used in the pixel present in the first line group and the detection signal amount used in the pixel present in the second line group.

11. The endoscope apparatus according to claim 8, wherein, for a horizontal pixel line where the illumination light is switched within an exposure period of each horizontal pixel line of the first and second exposure frames, a first period from an exposure start timing of the horizontal pixel line to a switching timing of the illumination light and a second period from the switching timing of the illumination light to an exposure end timing of the horizontal pixel line are determined according to a shift of the exposure start timing with respect to the horizontal pixel line of the rolling shutter.

12. The endoscope apparatus according to claim 8, wherein the plurality of types of illumination light beams include white illumination light and narrowband wavelength light having a narrower waveguide width than the white illumination light.

13. The endoscope apparatus according to claim 8, wherein the plurality of types of illumination light beams include at least red light, green light, and blue light.

14. The endoscope apparatus according to claim 1, wherein, when performing scan driving sequentially from one end side of the horizontal pixel line in a vertical direction to the other end side, the imaging unit performs driving by shifting an exposure start timing of each horizontal pixel line so that an exposure end timing of the horizontal pixel line on the other end side matches an exposure start timing of the horizontal pixel line on the one end side in a next frame.

15. The endoscope apparatus according to claim 14, wherein the imaging signal generation unit sets a line bisecting a horizontal pixel line group, which includes a horizontal pixel line on the one end side in the vertical direction to a horizontal pixel line of an exposure start timing that matches an exposure end timing of the horizontal pixel line, in the vertical direction as a division line, divides this horizontal pixel line group into a first line group on the one end side in the vertical direction and a second line group on the other end side with the division line as a boundary, and generates the imaging signal amount by changing the detection signal amount used in the pixel present in the first line group and the detection signal amount used in the pixel present in the second line group.

16. The endoscope apparatus according to claim 1, wherein, for a horizontal pixel line where the illumination light is switched within an exposure period of each horizontal pixel line of the first and second exposure frames, a first period from an exposure start timing of the horizontal pixel line to a switching timing of the illumination light and a second period from the switching timing of the illumination light to an exposure end timing of the horizontal pixel line are determined according to a shift of the exposure start timing with respect to the horizontal pixel line of the rolling shutter.

17. The endoscope apparatus according to claim 1, wherein the plurality of types of illumination light beams include white illumination light and narrowband wavelength light having a narrower waveguide width than the white illumination light.

18. The endoscope apparatus according to claim 1, wherein the plurality of types of illumination light beams include at least red light, green light, and blue light.

19. The endoscope apparatus according to claim 1, wherein the light source is formed by a semiconductor light emitting element.

* * * * *